US006444669B1

United States Patent
Jaehne et al.

(10) Patent No.: US 6,444,669 B1
(45) Date of Patent: Sep. 3, 2002

(54) 8,8A-DIHYDROINDENO[1,2-D]THIAZOLE DERIVATIVES WHICH CARRY IN THE 2-POSITION A SUBSTITUENT HAVING A SULFONAMIDE STRUCTURE OR SULFONE STRUCTURE; PROCESSES FOR THEIR PREPARATION AND THEIR USE AS MEDICAMENTS

(75) Inventors: Gerhard Jaehne, Frankfurt; Hans Jochen Lang; Matthias Gossel, both of Hofheim; Martin Bickel, Bad Homburg, all of (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 10/046,989

(22) Filed: Jan. 17, 2002

Related U.S. Application Data

(62) Division of application No. 09/792,049, filed on Feb. 26, 2001, now Pat. No. 6,352,987.

(30) Foreign Application Priority Data

Feb. 26, 2000 (DE) .......................................... 100 09 311

(51) Int. Cl.⁷ .................... A61K 31/535; A61K 31/425; A61K 31/53
(52) U.S. Cl. ................. 514/232.5; 514/366; 514/232.8; 514/241; 514/254.02; 514/255.01
(58) Field of Search .............................. 514/232.5, 366, 514/232.8, 241, 254.02, 255.01

(56) References Cited

U.S. PATENT DOCUMENTS

| 4,174,397 | A | | 11/1979 | Knabe et al. | |
|---|---|---|---|---|---|
| 6,090,833 | A | * | 6/2000 | Jaehne et al. | ............... 514/366 |

FOREIGN PATENT DOCUMENTS

| AT | 365181 | 12/1981 |
|---|---|---|
| WO | WO00/51997 A1 | 9/2000 |

OTHER PUBLICATIONS

Taylor, E. C. et al., "A New Synthesis of Aliphatic and Aromatic Thioamides from Nitriles", J. Am. Chem. Soc., 1960, pp. 2656–2657, vol. 82.

Hurd, R. N. et al., "The Preparation and Chemical Properties of Thionamides", Chem. Rev., 1961, pp. 45–86, vol. 61.

Scheibye, S. et al., "Studies on Organophosphorus Compounds XXI. The Dimer of p–methoxyphenylthionophospine Sulfide as Thiation Reagent. A New Route to Thiocarboxamides", Bull. Soc. Chim. Belg., 1978, pp. 229–238, vol. 87, No. 3.

Tyle, P., "Iontophoretic Devices for Drug Delivery", Pharmaceutical Research, 1986, pp. 318, vol. 3, No. 6, Plenum Publishing Corporation.

* cited by examiner

Primary Examiner—Theodore J. Criares
Assistant Examiner—Jennifer Kim
(74) Attorney, Agent, or Firm—Heller Ehrman White and McAuliffe

(57) ABSTRACT

8,8a-Dihydroindeno[1,2-d]thiazole derivatives which carry in the 2-position a substituent having a sulfonamide structure or sulfone structure; processes for their preparation and their use as medicaments The invention relates to polycyclic dihydrothiazoles and to their physiologically acceptable salts and physiologically functional derivatives.

Compounds of formula I,

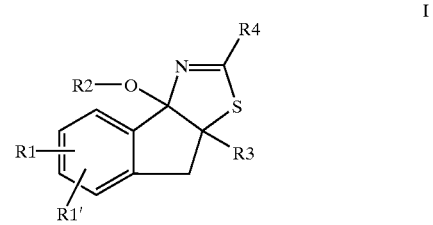

in which the radicals are as defined above, and their physiologically acceptable salts and processes for their preparation are described. The compounds are suitable, for example, as anorectics.

12 Claims, No Drawings

8,8A-DIHYDROINDENO[1,2-D]THIAZOLE DERIVATIVES WHICH CARRY IN THE 2-POSITION A SUBSTITUENT HAVING A SULFONAMIDE STRUCTURE OR SULFONE STRUCTURE; PROCESSES FOR THEIR PREPARATION AND THEIR USE AS MEDICAMENTS

This application is a division of Ser. No. 09/792,049, filed Feb. 26, 2001, now U.S. Pat. No. 6,352,987 and claims priority to German Application No. 10009311.6 filed Feb. 26, 2000, the entire contents of which are hereby incorporated by reference.

FIELD OF THE INVENTION

The invention relates to polycyclic dihydrothiazoles and to their physiologically acceptable salts and physiologically functional derivatives.

BACKGROUND OF THE INVENTION

Thiazolidine derivatives having anorectic action have been described in the prior art (Austrian Patent No. 365181).

The object of the invention is to provide compounds having a therapeutically useful anorectic action.

SUMMARY OF THE INVENTION

The invention relates to compounds of formula I:

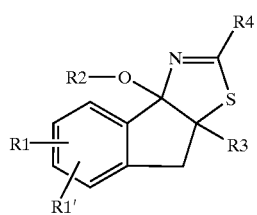

in which

R1, R1' are independently selected from H, F, Cl, Br, I, $CF_3$, $NO_2$, CN, COOH, COO($C_1$–$C_6$)-alkyl, $CONH_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-akynyl, O—($C_1$–$C_6$)-alkyl, wherein one or more of the hydrogens of the alkyl radicals may be replaced by fluorine, or one hydrogen may be replaced by OH, $OC(O)CH_3$, OC(O)H, O—$CH_2$—Ph, $NH_2$, NH—CO—$CH_3$ or N(COOCH$_2$Ph)$_2$;

$SO_2$—$NH_2$, $SO_2NH(C_1$–$C_6)$-alkyl, $SO_2N[(C_1$–$C_6)$-alkyl]$_2$, S—($C_1$–$C_6$)-alkyl, S—$(CH_2)_n$-phenyl, SO—($C_1$–$C_6$)-alkyl, SO—$(CH_2)_n$-phenyl, $SO_2$—($C_1$–$C_6$)-alkyl, $SO_2$—$(CH_2)_n$-phenyl, wherein n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$;

$NH_2$, NH—($C_1$–$C_6$)-alkyl, N[($C_1$–$C_6$)-alkyl]$_2$, NH($C_1$–$C_7$)-acyl, phenyl, biphenylyl, O—$(CH_2)_n$-phenyl, where n is 0–6, 1- or 2-naphthyl, 2-, 3- or 4-pyridyl, 2- or 3-furanyl or 2- or 3-thienyl, wherein any of the phenyl, biphenylyl, naphthyl, pyridyl, furanyl or thienyl rings may be substituted one to three times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N[($C_1$–$C_6$)-alkyl]$_2$, $SO_2$—$CH_3$, COOH, COO—($C_1$–$C_6$)-alkyl or $CONH_2$;

1,2,3-triazol-5-yl, where the triazole ring may be substituted in the 1-, 2- or 3-position by methyl or benzyl; or tetrazol-5-yl, where the tetrazole ring may be substituted in the 1- or 2-position by methyl or benzyl;

R2 is H, ($C_1$–$C_6$)-alkyl, ($C_3$–$C_6$)-cycloalkyl, $(CH_2)_n$-phenyl, $(CH_2)_n$-thienyl, $(CH_2)_n$-pyridyl, $(CH_2)_n$-furyl, C(O)—($C_1$–$C_6$)-alkyl, C(O)—($C_3$–$C_6$)-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl, wherein n is 0–5 and in which any of phenyl, thienyl, pyridyl and furyl may be substituted up to two times by Cl, F, CN, $CF_3$, ($C_1$–$C_3$)-alkyl, OH or O—($C_1$–$C_6$)-alkyl;

R3 is H, ($C_1$–$C_6$)-alkyl, F, CN, $N_3$, O—($C_1$–$C_6$)-alkyl, $(CH_2)_n$-phenyl, $(CH_2)_n$-thienyl, $(CH_2)_n$-pyridyl, $(CH_2)_n$-furyl, wherein n is 0–5 and in which any of phenyl, thienyl, pyridyl and furyl may be substituted up to two times by Cl, F, CN, $CF_3$, ($C_1$–$C_3$)-alkyl, OH or O—($C_1$–$C_6$)-alkyl;

$OC(O)CH_3$, ($C_2$–$C_6$)-alkynyl, ($C_2$–$C_6$)-alkenyl, COO($C_1$–$C_6$)-alkyl, C(O)OH, $C(O)NH_2$, $C(O)NHCH_3$ or $C(O)N(CH_3)_2$;

R4 is $(CH_2)_n$—R5, wherein n is 0–6;

R5 is phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl;

and R5 is substituted by

NH—$SO_2$—($C_1$–$C_6$)-alkyl or NH—$SO_2$-phenyl, wherein the phenyl ring may be substituted up to two times by F, Cl, CN, OH, ($C_1$–$C_6$)-alkyl, O—($C_1$–$C_6$)-alkyl, $CF_3$, COOH, COO($C_1$–$C_6$)-alkyl, $CONH_2$, $(CH_2)_n$—$SO_2$—($C_1$–$C_6$)-alkyl, where n is 1–6, $(CH_2)_m$—$SO_2$—$NH_2$, $(CH_2)_m$—$SO_2$—NH—($C_1$–$C_6$)-alkyl, $(CH_2)_m$—$SO_2$—N[($C_1$–$C_6$)-alkyl]$_2$ or $(CH_2)_m$—$SO_2$—N(=CH—N(CH$_3$)$_2$), wherein m is 0–6;

and R5 may be further substituted by F, Cl, Br, OH, $CF_3$, $NO_2$, CN, $OCF_3$, O—($C_1$–$C_6$)-alkyl, S—($C_1$–$C_6$)-alkyl, SO—($C_1$–$C_6$)-alkyl, ($C_1$–$C_6$)-alkyl, ($C_3$–$C_6$)-cycloalkyl, COOH, COO($C_1$–$C_6$)-alkyl, COO($C_3$–$C_6$)-cycloalkyl, $CONH_2$, CONH($C_1$–$C_6$)-alkyl, CON[($C_1$–$C_6$)-alkyl]$_2$, CONH($C_3$–$C_6$)-cycloalkyl, $NH_2$, NH—CO—($C_1$–$C_6$)-alkyl, NH—CO-phenyl, pyrrolidin-1-yl, morpholin-1-yl, piperidin-1-yl, piperazin-1-yl, 4-methylpiperazin-1-yl, $(CH_2)_n$-phenyl, O—$(CH_2)_n$-phenyl, S—$(CH_2)_n$-phenyl or $SO_2$—$(CH_2)_n$-phenyl, wherein n is 0–3;

and their physiologically acceptable salts and physiologically functional derivatives.

The invention also relates to pharmaceutical compositions containing the compounds of formula I and pharmaceutically acceptable carriers. Also, pharmaceutical compositions containing the compounds of formula I in combination with at least one additional anorectic agents are contemplated. The invention envisages treatment of obesity via administration of compounds of formula I. Methods of treatment for type II diabetes and methods of enhancing lipid metabolism are also contemplated.

DETAILED DESCRIPTION OF THE INVENTION

The invention is directed to polycyclic thiazole compounds which are anorectics and are useful in the treatment of type II diabetes and obesity. The compounds have general formula (I):

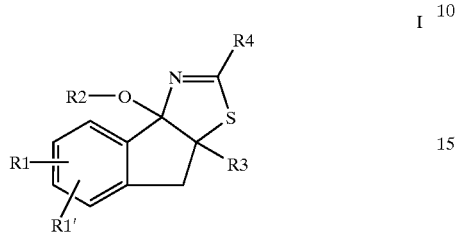

in which

R1, R1' are independently selected from H, F, Cl, Br, I, $CF_3$, $NO_2$, CN, COOH, $COO(C_1–C_6)$-alkyl, $CONH_2$, $CONH(C_1–C_6)$-alkyl, $CON[(C_1–C_6)$-alkyl$]_2$, $(C_1–C_6)$-alkyl, $(C_2–C_6)$-alkenyl, $(C_2–C_6)$-alkynyl, $O—(C_1–C_6)$-alkyl, wherein one or more of the hydrogens of the alkyl radicals may be replaced by fluorine, or one hydrogen may be replaced by OH, $OC(O)CH_3$, OC(O)H, $O—CH_2—Ph$, $NH_2$, $NH—CO—CH_3$ or $N(COOCH_2Ph)_2$;

$SO_2—NH_2$, $SO_2NH(C_1–C_6)$-akyl, $SO_2N[(C_1–C_6)$-alkyl$]_2$, $S—(C_1–C_6)$-alkyl, $S—(CH_2)_n$-phenyl, $SO—(C_1–C_6)$-alkyl, $SO—(CH_2)_n$-phenyl, $SO_2—(C_1–C_6)$-alkyl, $SO_2$-$(CH_2)$-phenyl, wherein n is 0–6 and the phenyl radical may be substituted up to two times by F, Cl, Br, OH, $CF_3$, $NO_2$, CN, $OCF_3$, $O—(C_1–C_6)$-alkyl, $(C_1–C_6)$-alkyl or $NH_2$;

$NH_2$, $NH—(C_1–C_6)$-alkyl, $N[(C_1–C_6)$-alkyl$]_2$, $NH(C_1–C_7)$-acyl, phenyl, biphenylyl, $O—(CH_2)_n$-phenyl, where n is 0–6, 1- or 2-naphthyl, 2-, 3- or 4pyridyl, 2- or 3-furanyl or 2- or 3-thienyl, wherein any of the phenyl, biphenylyl, naphthyl, pyridyl, furanyl or thienyl rings may be substituted one to three times by F, Cl, Br, I, OH, $CF_3$, $NO_2$, CN, $OCF_3$, $O—(C_1–C_6)$-alkyl, $(C_1–C_6)$-alkyl, $NH_2$, $NH(C_1–C_6)$-alkyl, $N[(C_1–C_6)$-alkyl$]_2$, $SO_2—CH_3$, COOH, COO—$(C_1–C_6)$-alkyl or $CONH_2$;

1,2,3-triazol-5-yl, where the triazole ring may be substituted in the 1-, 2- or 3-position by methyl or benzyl; or tetrazol-5-yl, where the tetrazole ring may be substituted in the 1- or 2-position by methyl or benzyl;

R2 is H, $(C_1–C_6)$-alkyl, $(C_3–C_6)$-cycloalkyl, $(CH_2)_n$-phenyl, $(CH_2)_n$-thienyl, $(CH_2)_n$-pyridyl, $(CH_2)_n$-furyl, $C(O)—(C_1–C_6)$-alkyl, $C(O)—(C_3–C_6)$-cycloalkyl, $C(O)—(CH_2)_n$-phenyl, $C(O)—(CH_2)_n$-thienyl, $C(O)—(CH_2)_n$-pyridyl or $C(O)—(CH_2)_n$-furyl, wherein n is 0–5 and in which any of phenyl, thienyl, pyridyl and furyl may be substituted up to two times by Cl, F, CN, $CF_3$, $(C_1–C_3)$-alkyl, OH or $O—(C_1–C_6)$-alkyl;

R3 is H, $(Cl–C_6)$-alkyl, F, CN, $N_3$, $O—(C_1–C_6)$-alkyl, $(CH_2)_n$-phenyl, $(CH_2)_n$-thienyl, $(CH_2)_n$-pyridyl, $(CH_2)_n$-furyl, wherein n is 0–5 and in which any of phenyl, thienyl, pyridyl and furyl may be substituted up to two times by Cl, F, CN, $CF_3$, $(C_1–C_3)$-alkyl, OH or O $(C_1–C_6)$-alkyl;

$OC(O)CH_3$, $(C_2–C_6)$-alkynyl, $(C_2–C_6)$-alkenyl, $COO(C_1–C_6)$-alkyl, C(O)OH, $C(O)NH_2$, $C(O)NHCH_3$ or $C(O)N(CH_3)_2$;

R4 is $(CH_2)_n$—R5, wherein n is 0–6;

R5 is phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl;

and R5 is substituted by $NH—SO—(C_1–C_6)$-alkyl or $NH—SO_2$-phenyl, wherein the phenyl ring may be substituted up to two times by F, Cl, CN, OH, $(C_1–C_6)$-alkyl, $O—(C_1–C_6)$-alkyl, $CF_3$, COOH, $COO(C_1–C_6)$-alkyl, $CONH_2$, $(CH_2)_n—SO_2—(C_1–C_6)$-alkyl, where n is 1–6, $(CH_2)_m—SO_2—NH_2$, $(CH_2)_m—SO_2—NH—(C_1–C_6)$-alkyl, $(CH_2)_m—SO_2—N[(C_1–C_6)$-alkyl$]_2$ or $(CH_2)_m—SO_2—N(=CH—N(CH_3)_2)$, wherein m is 0–6;

and R5 may be further substituted by F, Cl, Br, OH, $CF_3$, $NO_2$, CN, $OCF_3$, $O—(C_1–C_6)$-alkyl, $S—(C_1–C_6)$-alkyl, $SO—(C_1–C_6)$-alkyl, $(C_1–C_6)$-alkyl, $(C_3–C_6)$-cycloalkyl, COOH, $COO(C_1–C_6)$-alkyl, $COO(C_3–C_6)$-cycloalkyl, $CONH_2$, $CONH(C_1–C_6)$-alkyl, $CON[(C_1–C_6)$-alkyl$]_2$, $CONH(C_3–C_6)$-cycloalkyl, $NH_2$, $NH—CO—(C_1–C_6)$-alkyl, NH—CO-phenyl, pyrrolidin-1-yl, morpholin-1-yl, piperidin-1-yl, piperazin-1-yl, 4-methylpiperazin-1-yl, $(CH_2)_n$-phenyl, $O—(CH_2)_n$-phenyl, $S—(CH_2)_n$-phenyl or $SO_2—(CH_2)_n$-phenyl, wherein n is 0–3;

and their physiologically acceptable salts and physiologically functional derivatives.

In a preferred embodiment, the compounds of formula I are where

R1, R1' are independently selected from H, F, Cl, Br, I, $CF_3$, $NO_2$, CN, COOH, $COO(C_1–C_6)$-alkyl, $CONH_2$, $CONH(C_1–C_6)$-alkyl, $CON[(C_1–C_6)$-alkyl$]_2$, $(C_1–C_6)$-alkyl, $(C_2–C_6)$-alkenyl, $(C_2–C_6)$-alkynyl, $O—(C_1–C_6)$-alkyl, wherein one hydrogen of the alkyl radicals may be replaced by OH, $OC(O)CH_3$, OC(O)H, $O—CH_2—Ph$, $NH_2$, $NH—CO—CH_3$ or $N(COOCH_2Ph)_2$;

$SO_2—NH_2$, $SO_2NH(C_1–C_6)$-alkyl, $SO_2N[(C_1–C_6)$-alkyl$]_2$, $S—(C_1–C_6)$-akyl, $S—(CH_2)_n$-phenyl, $SO—(C_1–C_6)$-alkyl, $SO—(CH_2)_n$-phenyl, $SO_2$-$(C_1–C_6)$-alkyl, $SO_2$-$(CH_2)_n$-phenyl, wherein n is 0–6 and the phenyl radical may be substituted up to two times by F, Cl, Br, OH, $CF_3$, $NO_2$, CN, $OCF_3$, $O—(C_1–C_6)$-alkyl, $(C_1–C_6)$-alkyl or $NH_2$;

$NH_2$, $NH—(C_1–C_6)$-alkyl, $N[(C_1–C_6)$-alkyl$]_2$, $NH(C_1–C_7)$-acyl, phenyl, biphenylyl, $O—(CH_2)_n$-phenyl, wherein n is 0–6, 1- or 2-naphthyl, 2-, 3- or 4pyridyl, 2- or 3-furanyl or 2- or 3-thienyl wherein any of the phenyl, biphenylyl, naphthyl, pyridyl, furanyl or thienyl rings may be substituted one to 3 times by F, Cl, Br, I, OH, $CF_3$, $NO_2$, CN, $OCF_3$, $O—(C_1–C_6)$-alkyl, $(C_1–C_6)$-alkyl, $NH_2$, $NH(C_1–C_6$-alkyl, $N[(C_1–C_6)$-alkyl$]_2$, $SO_2—CH_3$, COOH, COO—$(C_1–C_6)$-alkyl or $CONH_2$;

1,2,3-triazol-5-yl, where the triazole ring may be substituted in the 1-, 2- or 3-position by methyl or benzyl; or tetrazol-5-yl, where the tetrazole ring may be substituted in the 1- or 2-position by methyl or benzyl;

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, $C(O)-(C_1-C_6)$-alkyl, $C(O)-(C_3-C_6)$-cycloalkyl, $C(O)-(CH_2)_n$-phenyl, $C(O)-(CH_2)_n$-thienyl, $C(O)-(CH_2)_n$-pyridyl or $C(O)-(CH)_n$-furyl,
wherein n is 0–5 and in which any of phenyl, thienyl, pyridyl and furyl may be substituted up to two times by Cl, F, CN, $CF_3$, $(C_1-C_3)$-alkyl, OH or $O-(C_1-C_6)$-alkyl;

R3 is H, $(C_1-C_6)$-alkyl, F, CN, $N_3$, $O-(C_1-C_6)$-alkyl, $(CH_2)_n$-phenyl, $(CH_2)_n$-thienyl, $(CH_2)_n$-pyridyl, $(CH_2)_n$-furyl,
wherein n is 0–5 and in which any of phenyl, thienyl, pyridyl and furyl may be substituted up to two times by Cl, F, CN, $CF_3$, $(C_1-C_3)$-alkyl, OH or $O-(C_1-C_6)$-alkyl;
$OC(O)CH_3$, $(C_2-C_6)$-alkynyl, $(C_2-C_6)$-alkenyl, COO $(C_1-C_6)$-alkyl, $C(O)OH$, $C(O)NH_2$, $C(O)NHCH_3$ or $C(O)N(CH_3)_2$;

R4 is $(CH_2)_n$—R5, wherein n is 0–6;

R5 is phenyl, biphenylyl, 1- or 2-naphthyl, 2-, 3- or 4-pyridyl or 2- or 3-thienyl;

and R5 is substituted by
$NH-SO_2-(C_1-C_6)$-alkyl, $NH-SO_2$-phenyl,
wherein the phenyl ring may be substituted up to two times by F, Cl, CN, OH, $(C_1-C_6)$-alkyl, $O-(C_1-C_6)$-alkyl, $CF_3$, COOH, $COO(C_1-C_6)$-alkyl, $CONH_2$;
$(CH_2)_n-SO_2-(C_1-C_6)$-alkyl, wherein n is 1–6, $(CH_2)_m-SO_2-NH_2$, $(CH_2)_m-SO_2-NH-(C_1-C_6)$-alkyl, $(CH_2)_m-SO_2-N[(C_1-C_6)$-alkyl$]_2$ or $(CH_2)_m-SO_2-N(=CH-N(CH_3)_2)$, wherein m is 0–6;

and R5 may be further substituted by F, Cl, Br, OH, $CF_3$, CN, $OCF_3$, $O-(C_1-C_6)$-alkyl, $(C_1-C_6)$-alkyl, $(C_3-C_6)$ cycloalkyl, COOH, $COO(C_1-C_6)$-alkyl, $COO(C_3-C_6)$-cycloalkyl, $CONH_2$, $CONH(C_1-C_6)$-alkyl, CON $[(C_1-C_6)$-alkyl$]_2$, $NH_2$, $NH-CO-(C_1-C_6)$-alkyl, NH—CO-phenyl, $(CH_2)_n$-phenyl, $O-(CH_2)_n$-phenyl, $S-(CH_2)_n$-phenyl, $SO_2-(CH_2)_n$-phenyl, wherein n is 0–3;

and their physiologically acceptable salts and physiologically functional derivatives.

In a particularly preferred embodiment, the compounds of formula I are where

R1, R1' are independently selected from H, F, Cl, Br, I, $CF_3$, $NO_2$, CN, COOH, $COO(C_1-C_6)$-alkyl, $CONH_2$, $(C_1-C_6)$-alkyl, $(C_2-C_6)$-alkenyl, $(C_2-C_6)$-alkynyl, $O-(C_1-C_6)$-alkyl, $SO_2-NH_2$, phenyl or $O-(CH_2)_n$-phenyl,
wherein n is 0–6, wherein any of the phenyl rings may be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$ or $CONH_2$;

R2 is H, $(C_1-C_6)$-alkyl, $(C_3-C_6)$-cycloalkyl, $(CH_2)_n$-phenyl, $C(O)-(C_1-C_6)$-alkyl or $C(O)-(CH_2)_n$-phenyl,
wherein n is 0–5 and in which phenyl may be substituted up to two times by Cl, F, CN, $CF_3$, $(C_1-C_3)$-alkyl, OH or $O-(C_1-C_6)$-alkyl;

R3 is H, $(C_1-C_6)$-alkyl, F, $(CH_2)_n$-phenyl,
wherein n is 0–5 and in which phenyl may be substituted up to two times by Cl, F, CN, $CF_3$, $(C_1-C_3)$-alkyl, OH or $O-(C_1-C_6)$-alkyl;
$COO(C_1-C_6)$-alkyl, $C(O)OH$ or $C(O)NH_2$;

R4 is $(CH_2)_n$—R5, wherein n is 0–6; or

R5 is phenyl, 1- or 2-naphthyl;

and R5 is substituted by
$NH-SO_2-(C_1-C_6)$-alkyl, $NH-SO_2$-phenyl,
wherein the phenyl ring may be substituted up to two times by F, Cl, CN, OH, $(C_1-C_6)$-alkyl, $O-(C_1-C_6)$-alkyl, $CF_3$, COOH, $COO(C_1-C_6)$-alkyl or $CONH_2$;
$(CH_2)_n-SO_2-(C_1-C_6)$-alkyl,
wherein n is 1–6,
$(CH_2)_m-SO_2-NH_2$, $(CH_2)_m-SO_2-NH-(C_1-C_6)$-alkyl, $(CH_2)_m-SO_2N[(C_1-C_6)$-alkyl$]_2$ or $(CH_2)_m-SO_2-N(=CH-N(CH_3)_2)$,
wherein m is 0–6;

and R5 may further be substituted by F, Cl, Br, OH, $CF_3$, CN, $OCF_3$, $O-(C_1-C_6)$-alkyl, $(C_1-C_6)$-alkyl, COOH, $COO(C_1-C_6)$-alkyl, $CONH_2$, $NH_2$, $NH-CO-(C_1-C_6)$-alkyl, NH—CO-phenyl, $(CH_2)_n$-phenyl, $O-(CH_2)_n$-phenyl or $SO_2-(CH_2)_n$-phenyl,
wherein n is 0–3;

and their physiologically acceptable salts.

The invention relates to compounds of formula I, in the form of their racemates, racemic mixtures and pure enantiomers, and to their diastereomers and mixtures thereof.

The alkyl, alkenyl and alkynyl radicals in the substituents R1, R1', R2, R3 and R5 may be either straight-chain or branched.

Pharmaceutically acceptable salts are particularly suitable for medicinal applications compared with the starting materials or base compounds, due to their higher water solubility. These salts must have a pharmaceutically acceptable anion or cation. Suitable pharmaceutically acceptable acid addition salts of the compounds according to the invention are salts of inorganic acids, such as hydrochloric acid, hydrobromic acid, phosphoric acid, metaphosphoric acid, nitric acid, sulfonic acid and sulfuric acid, and of organic acids, such as, for example, acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid. For medicinal purposes, the chlorine salt is particularly preferred. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically unacceptable anion are likewise included in the scope of the invention as useful intermediates for the production or purification of pharmaceutically acceptable salts and/or for use in nontherapeutic, for example in-vitro, applications.

The term "physiologically functional derivative" used here relates to any physiologically acceptable derivative of a compound of formula I according to the invention, for example an ester, which, on administration to a mammal, such as, for example, man, is able (directly or indirectly) to form a compound of formula I or an active metabolite thereof.

The physiologically functional derivatives also include prodrugs of the compounds according to the invention. Such prodrugs are able to be metabolized in vivo to a compound according to the invention. These prodrugs can themselves be active or inactive.

The compounds according to the invention may also be present in various polymorphic forms, for example as amorphous and crystalline polymorphic forms. All polymorphic forms of the compounds according to the invention are included in the scope of the invention and are a further aspect of the invention.

Hereinbelow, all references to "compound(s) according to formula (I)" refer to compounds of formula (I) as described above, and to their salts, solvates and physiologically functional derivatives as described herein.

The amount of a compound according to formula (I) which is necessary in order to achieve the desired biological effect is dependent on a number of factors, for example the specific compound selected, the intended use, the manner of administration and the clinical condition of the patient. In general, the daily dose is in the range from 0.3 mg to 100 mg (typically from 3 mg to 50 mg) per day per kilogram of body weight, for example 3–10 mg/kg/day. An intravenous dose may be, for example, in the range from 0.3 mg to 1.0 mg/kg, which may be suitably administered as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampoules for injections may contain, for example, from 1 mg to 100 mg, and orally administrable individual dose formulations, such as, for example, tablets or capsules, may contain, for example, from 1.0 to 1000 mg, typically from 10 to 600 mg. In the case of pharmaceutically acceptable salts, the abovementioned weight details relate to the weight of the dihydrothiazolium ion derived from the salt. For the prophylaxis or therapy of the abovementioned conditions, the compounds according to formula (I) may be used themselves as the compound, but they are preferably present in the form of a pharmaceutical composition with a tolerable excipient. The excipient must of course be tolerable, in the sense that it is compatible with the other constituents of the composition and is not harmful to the patient's health. The excipient may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions according to the invention may be prepared by one of the known pharmaceutical methods, which essentially consist in mixing the constituents with pharmacologically acceptable excipients and/or auxiliaries.

Pharmaceutical compositions according to the invention are those which are suitable for oral, rectal, topical, peroral (e.g. sublingual) and parenteral (e.g. subcutaneous, intramuscular, intradermal or intravenous) administration, although the most suitable manner of administration in each individual case is dependent on the nature and severity of the condition to be treated and on the nature of the compound according to formula (I) used in each case. Sugar-coated formulations and sugar-coated delayed release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be present in separate units, such as, for example, capsules, cachets, lozenges or tablets which in each case contain a certain amount of the compound according to formula (I); as powders or granules; as solution or suspension in an aqueous or nonaqueous liquid; or as an oil-in-water or water-in-oil emulsion. As already mentioned, these compositions may be prepared by any suitable pharmaceutical method which includes a step in which the active compound and the excipient (which may consist of one or more additional constituents) are brought into contact. In general, the compositions are prepared by uniform and homogeneous mixing of the active compound with a liquid and/or finely divided solid excipient, after which the product is shaped, if necessary. Thus a tablet, for example, may be prepared by pressing or shaping a powder or granules of the compound, if appropriate with one or more additional constituents. Pressed tablets may be prepared by tableting the compound in free-flowing form, such as, for example, in a powder or, granules, if appropriate mixed with a binder, lubricant, inert diluent and/or one (a number of) surface-active/dispersing agent(s) in a suitable machine. Shaped tablets may be prepared by shaping the pulverulent compound, moistened with an inert liquid diluent, in a suitable machine.

Pharmaceutical compositions which are suitable for peroral (sublingual) administration include lozenges which contain a compound according to formula (I) with a flavoring, customarily sucrose and gum arabic or tragacanth, and pastilles which include the compound in an inert base such as gelatin and glycerol or sucrose and gum arabic.

Suitable pharmaceutical compositions for parenteral administration preferably include sterile aqueous preparations of a compound according to formula (I), which are preferably isotonic with the blood of the intended recipient. These preparations are preferably administered intravenously, although the administration may also take place subcutaneously, intramuscularly or intradermally as an injection. These preparations may preferably be prepared by mixing the compound with water and rendering the obtained solution sterile and isotonic with the blood. Injectable compositions according to the invention in general contain from 0.1 to 5% by weight of the active compound.

Suitable pharmaceutical compositions for rectal administration are preferably present as individual dose suppositories. These may be prepared by mixing a compound according to formula (I) with one or more conventional solid excipients, for example cocoa butter, and shaping the resulting mixture.

Suitable pharmaceutical compositions for topical application to the skin are preferably present as ointment, cream, lotion, paste, spray, aerosol or oil. Excipients which may be used are petroleum jelly, lanolin, polyethylene glycols, alcohols and combinations of two or more of these substances. The active compound is in general present in a concentration of from 0.1 to 15%, for example of from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from about 1% to 35%, preferably from about 3% to 15%. As a particular possibility, the active compound may be released by electrotransport or iontophoresis, as described, for example, in Pharmaceutical Research, 2(6): 318 (1986).

The invention furthermore relates to a process for preparing the compounds of formula I, which comprises obtaining the compounds of formula I in such a way that the procedure is according to the following reaction scheme:

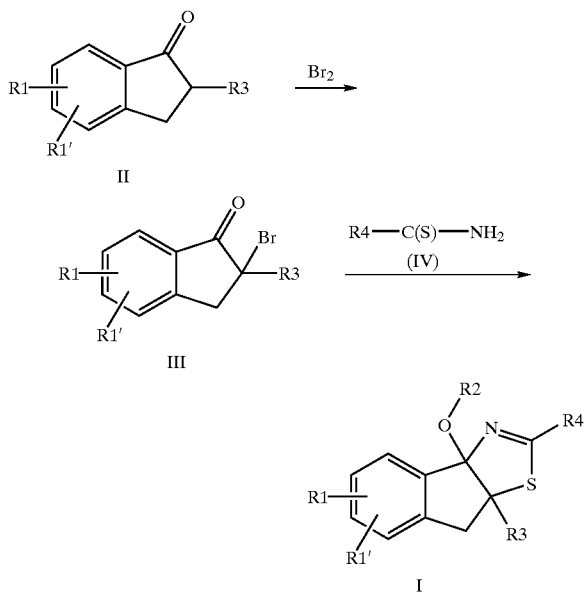

As part of the reaction scheme, compounds of formula II, formula II

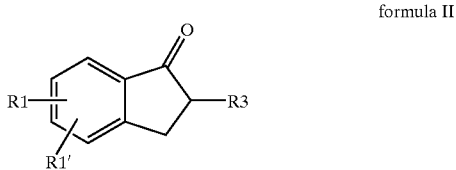

in which R1 and R1' are as defined above, are reacted with bromine to give a compound of formula III in which R3 is as defined for formula I.

Compounds of formula III are then reacted with thioamides of formula IV

IV

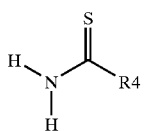

in which R4 is as defined for compounds of formula I in which R2 is hydrogen, For their part, these compounds may be converted by standard methods into compounds of formula I in which R2 is as defined for formula I.

The compounds of formula I may also be present as salts with acids. Suitable inorganic acids are, for example: hydrohalic acids, such as hydrochloric acid and hydrobromic acid, and also sulfuric acid, phosphoric acid and amidosulfonic acid. Organic acids which may be mentioned are, for example: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4(3H)-one 2,2-dioxide.

In the reaction scheme described above, it is advantageous to react the compounds of Formula III with the thioamides R4—C(S)—NH$_2$ in a molar ratio of from 1:1 to 1:1.5. The reaction is advantageously carried out in an inert solvent, for example in polar organic solvents, such as dimethylformamide, dimethylacetamide, N-methyl-2-pyrrolidone, dioxane, tetrahydrofuran, acetonitrile, nitromethane or diethylene glycol dimethyl ether. Particularly advantageous solvents, however, have proved to be methyl acetate and ethyl acetate, short-chain alcohols, such as methanol, ethanol, propanol, isopropanol, and lower dialkyl ketones, such as, for example, acetone, butan-2-one or hexan-2-one. Mixtures of the reaction media mentioned may also be used; and mixtures of the solvents mentioned with solvents which, taken per se, are less suitable, such as, for example, mixtures of methanol with benzene, ethanol with toluene, methanol with diethyl ether or with tert-butyl methyl ether, ethanol with carbon tetrachloride, acetone with chloroform, dichloromethane or 1,2-dichloroethane, may also be used, where the more polar solvent in each case should be used in an excess. The reactants may be suspended or dissolved in the respective reaction medium. In principle, the reactants may also be reacted in the absence of a solvent, in particular if the respective thioamide has a melting point which is as low as possible. The reaction proceeds in an only slightly exothermic manner and may be carried out between −10° C. and 150° C., preferably between 30° C. and 100° C. A temperature range between 50° C. and 90° C. has generally been found to be particularly favorable.

The reaction time is largely dependent on the reaction temperature and is between 2 minutes and 3 days at relatively high and relatively low temperatures, respectively. In the favorable temperature range, the reaction time is generally between 5 minutes and 48 hours.

In the course of the reaction, the compounds of formula I frequently form a poorly soluble deposit in the form of their acid addition salts, a suitable precipitating agent is additionally subsequently added. Those used are, for example, hydrocarbons such as benzene, toluene, cyclohexane or heptane or carbon tetrachloride; in particular, alkyl acetates, such as ethyl acetate or n-butyl acetate, or dialkyl ethers, such as diethyl ether, diisopropyl ether, di-n-butyl ether or tert-butyl methyl ether prove particularly suitable. If the reaction mixture remains in solution after the end of the reaction, the salts of the compounds of formula I may be precipitated using one of the precipitating agents mentioned, if appropriate after concentration of the reaction solution. Furthermore, the solution of the reaction mixture may also be advantageously filtered into the solution of one of the precipitating agents mentioned, with stirring. Work-up of the reaction mixture may also be carried out such that the reaction mixture is rendered alkaline by addition of an organic base, such as, for example, triethylamine or diisobutylamine or ammonia or morpholine or piperidine or 1,8-diazabicyclo[5.4.0]undec-7-ene, and the crude reaction product is purified chromatographically, for example on a silica gel column, after concentration. Suitable eluents for this prove to be, for example, mixtures of ethyl acetate with methanol, mixtures of dichloromethane with methanol, mixtures of toluene with methanol or ethyl acetate or mixtures of ethyl acetate with hydrocarbons such as heptane. If the purification of the crude product is carried out in the manner last described, an acid addition product of formula I may be obtained from the pure base of formula I thus obtained by dissolving or suspending the base in an organic protic solvent, such as methanol, ethanol, propanol or isopropanol, or in an organic aprotic solvent, such as ethyl acetate, diethyl ether, diisopropyl ether, tert-butyl methyl ether, dioxane, tetrahydrofuran, acetone or butan-2-one, and then treating this mixture with an at least equimolar amount of an inorganic acid such as, for example, hydrochloric acid, dissolved in an inert solvent such as, for example, diethyl ether or ethanol, or another of the inorganic or organic acids mentioned further above.

The compounds of formula I may be recrystallized from an inert suitable solvent such as, for example, acetone, butan-2-one, acetonitrile or nitromethane. However, particularly advantageous is the precipitation from a solvent such as, for example, dimethylformamide, dimethylacetamide, nitromethane, acetonitrile, preferably methanol or ethanol.

The reaction of the compounds of formula III with the thioamides of formula IV may also be carried out such that an at least equimolar amount of a base, such as, for example, triethylamine, is added to the reaction mixture and the resulting compounds I are then optionally converted into their acid addition products.

By treatment with bases, the acid addition products I may be converted into the compounds of formula I (free base). Suitable bases are, for example, solutions of inorganic hydroxides, such as lithium hydroxide, sodium hydroxide, potassium hydroxide, calcium hydroxide or barium hydroxide, carbonates or hydrogen carbonates, such as sodium carbonate or potassium carbonate, sodium hydrogen carbonate or potassium hydrogen carbonate, ammonia and amines, such as triethylamine, diisopropylamine, dicyclohexylamine, piperidine, morpholine, methyldicyclohexylamine.

Thioamides of formula IV are either commercially available or may be obtained, for example, by reaction of the corresponding carboxamide with phosphorus pentasulfide in pyridine (R. N. Hurd, G. Delameter, Chem. Rev. 61, 45 (1961)), or with Lawesson's reagent in toluene, pyridine, hexamethylphosphoric triamide [Scheibye, Pedersen and Lawesson: Bull. Soc. Chim. Belges 87, 229 (1978)], preferably in a mixture of tetrahydrofuran with 1,3dimethyl-3, 4,5,6-tetrahydro-2(1H)-pyrimidinone or 1,3-dimethyl-2-imidazolidinone. Hydroxyl, amino or additional carbonyl functions are in this case protected using a removable protective function, such as, for example, a benzyl, tert-butyloxycarbonyl or benzyloxycarbonyl radical, or converted into an optionally cyclic acetal. Methods for this are described, for example, in Th. W. Greene and P. G. M. Wuts, Protective Groups in Organic Synthesis, Second Edition, 1991, John Wiley & Sons, New York.

Thioamides of formula IV may also be obtained by reacting nitriles of formula VII

formula VII with hydrogen sulfide (Houben-Weyl IX, 762) or thioacetamide (E. C. Taylor, J. A. Zoltewicz, J. Am. Chem. Soc. 82, 2656 (1960)) or O,O-diethyl dithiophosphoric acid. The reactions with hydrogen sulfide are preferably carried out in an organic solvent, such as methanol or ethanol, those with thioacetamide in a solvent such as dimethylformamide with addition of hydrochloric acid, and those with O,O-diethyl dithiophosphoric acid in a solvent such as ethyl acetate under acidic, e.g. HCl, conditions at room temperature or with warming.

The examples given below serve to illustrate the invention, but without restricting it. The measured melting or decomposition points (m.p.) were not corrected and are generally dependent on the heating rate.

TABLE 1

EXAMPLES

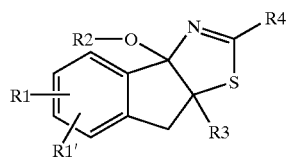

formula I

| Example | R1; R1' | R2 | R3 | R4 | Salt | m.p. [° C.] |
|---|---|---|---|---|---|---|
| 1 | 6-Cl; H | H | H | (C$_6$H$_4$)-4-NH-SO$_2$-(C$_6$H$_4$)-4-Cl | — | 116 |
| 2 | 6-Cl; H | H | H | (C$_6$H$_4$)-4-(NH-SO$_2$—CH$_3$) | — | 166 |
| 3 | 6-Cl; H | H | H | (C$_6$H$_3$)-3-(SO$_2$—N=CH—N(CH$_3$)$_2$)-4-Cl | — | 180 |
| 4 | 6-Cl; H | H | H | (C$_6$H$_3$)-3-(SO$_2$—NH$_2$)-4-Cl | — | 148 |
| 5 | 6-Cl; H | H | H | (C$_6$H$_4$)-4-(SO$_2$—NH$_2$) | — | 160 |
| 6 | H; H | H | H | (C$_6$H$_4$)-4-(SO$_2$—NH$_2$) | HBr | 250 |

The compounds of formula I are distinguished by favorable effects on lipid metabolism; in particular, they are suitable as anorectics. Other favorable effects on lipid metabolism include lowering cholesterol or low density lipoproteins (LDL) and increasing high density lipoproteins (HDL). The compounds may be employed on their own or in combination with other anorectically active compounds. Such further anorectically active compounds are mentioned, for example, in the Rote Liste, chapter 01 under slimming preparations/anorectics. Examples include, but are not limited to, DECORPA© (From Pierre Fabre Pharma, common name, sterculia), XENIXAL© (from Rocher, common name, orlistat), ANTIADIPOSITUM X-112S (from Haenseler, common name, D-norpseudoephedrin-HCl), FASUPOND© (from Eu Tho Arzneil, common name, D-norpseudoephedrin-HCl), MIRAPRONT© (from Mack, Illert., common name, D-norpseudoephedrin-Poly(styrol, divinylbenzol) sulfonate), REGENON© l-retard (from Temmler Pharma, common name, Amfepramon-HCl), RONDIMEN© (from ASTA Medica AWD, common name, Mefenorex-HCl), TENUATE© Retard (from Artegodan, common name, Amfepramon-HCl), VITA-SCHLANKTROPFEN SCHUCK (from Schuck, common name, D-norpseudoephedrine-HCl), VENCIPON© (from Artesan, common name, Ephedrin-HCL) CEFAMADAR©

(from Cefak, common name Nadar D4), and *Helianthus tuberosus* (Plantina). The compounds are suitable for the prophylaxis and in particular for the treatment of obesity. The compounds are furthermore suitable for the prophylaxis and in particular for the treatment of type II diabetes.

The efficacy of the compounds was tested as follows:
Biological Test Model:

The anorectic action was tested on male or female NMRI mice. After withdrawal of feed for 24 hours, the test preparation was administered via a stomach tube. Kept individually and with free access to drinking water, the animals were offered evaporated milk 30 minutes after the administration of the preparation. The consumption of evaporated milk was determined half-hourly for 3 hours and the general condition of the animals was observed. The measured milk consumption was compared with that of untreated control animals.

TABLE 2

Anorectic action, measured as reduction of the cumulated milk consumption of treated animals compared with untreated animals.

Compound/example formula I

| | Oral dose [mg/kg] | Number of animals/cumulated milk consumption of the treated animals N/[ml] | Number of animals/cumulated milk consumption of the untreated control animals N/[ml] | Reduction of the cumulated milk consumption in % of the control |
|---|---|---|---|---|
| Example 4 | 50 | female animals 5/0.82 | female animals 5/2.66 | 69 |
| Example 5 | 50 | male animals 5/0.08 | male animals 5/1.54 | 95 |
| Example 6 | 50 | male animals 5/1.26 | male animals 5/5.10 | 76 |

The data in the above table indicate that the compounds of formula I exhibit very good anorectic action.

The preparation of some examples is described in detail below; the other compounds of formula I were obtained in a similar manner:

EXAMPLE 1

Compound 1

4-Chloro-N-[4-(6-chloro-3a-hydroxy-8,8a-dihydro-3aH-indeno[1,2-d]thiazol-2yl)-phenyl]benzenesulfonamide a) 2-Bromo-5-chloroindan-1-one:

10 g (0.06 mol) of 5-chloroindan-1-one is dissolved with stirring at room temperature in 120 ml of glacial acetic acid. 0.05 ml of a 48% strength solution of HBr in water and then 3.074 ml (0.06 mol) of bromine, dissolved in 25 ml of glacial acetic acid, are added dropwise. The reaction completed after 2 h of stirring at room temperature as determined by thin layer chromatography (TLC). The solution of the crude product is, with stirring, slowly added dropwise to 300 ml of ice-water. The precipitated crude product is filtered off with suction and washed thoroughly with water. The moist residue is removed from the filter using ethyl acetate, and the phases of the filtrate are separated. The organic phase is dried over sodium sulfate, filtered and concentrated under reduced pressure. The residue is dissolved in 120 ml of hot n-heptane; the hot solution is filtered through a pleated filter and the solution is then left to crystallize at 0° C. The crystallized product is filtered off with suction and dried under reduced pressure.

M.P.: 94–96° C.

b) 4-(4-Chlorobenzenesulfonylamino)thiobenzamide:

0.26 g of 4-chloro-4'-cyanobenzenesulfonamide is suspended in 10 ml of absolute ethanol and admixed with 0.15 ml of diethyl dithiophosphate, and the mixture is stirred under reflux for 8 h. Another portion of 0.15 ml of diethyl dithiophosphate is then added, and the mixture is stirred at reflux temperature for a further 12 h. The cooled reaction mixture is concentrated under reduced pressure; the residue is stirred with dichloromethane and the solid residue is filtered off with suction, washed with dichloromethane and dried under reduced pressure. The resulting 4-(4-chlorobenzenesulfonylamino)thiobenzamide is used for the next step without any further purification.

c) 4-Chloro-N-[4-(6-chloro-3a-hydroxy-8,8a-dihydro-3aH-indeno[1,2d]thiazol-2-yl)phenyl]benzenesulfonamide:

At room temperature, 0.15 g of the compound from Example 1b and 0.11 g of the compound from Example 1a are dissolved in 5 ml of dry acetone, and the mixture is then stirred at room temperature for 4 h. 65 µl of triethylamine are added, and the mixture is stirred at room temperature overnight. Another 20 µl of triethylamine are added, and the mixture is stirred at room temperature for another night. The reaction mixture is then concentrated under reduced pressure; the residue is dissolved in ethyl acetate, washed twice with water and once with sat. sodium chloride solution, dried over magnesium sulfate, filtered and concentrated under reduced pressure. The residue is purified by silica gel chromatography using toluene/acetone 3/1. This gives 4-chloro-N-[4-(6-chloro- 3a-hydroxy-8,8a-dihydro-3aH-indeno[1,2-d]thiazol-2-yl)phenyl]benzenesulfonamide of melting point 116° C.

EXAMPLE 2

Compound 6

4-(6-Chloro-3a-hydroxy-8,8a-dihydro-3aH-indeno[1,2-d]thiazol-2-yl)benzenesulfonamide is prepared in a similar manner by reacting 2-bromo-5-chloroindan-1-one with 4-sulfamoylthiobenzamide. The compound has a melting point of 160° C.

What is claimed is:

1. A pharmaceutical composition, comprising one or more compounds of the following formula I:

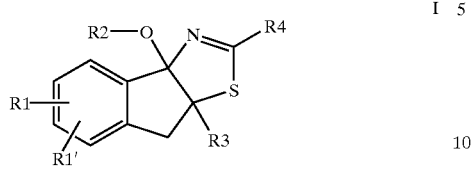

in which

R1, R1' are independently selected from H, F, Cl, Br, I, $CF_3$, $NO_2$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $O-(C_1-C_6)$-alkyl, wherein one or more of the hydrogens of the alkyl radicals may be replaced by fluorine, or one hydrogen may be replaced by OH, $OC(O)CH_3$, $OC(O)H$, $O-CH_2-Ph$, $NH_2$, $NH-CO-CH_3$ or $N(COOCH_2Ph)_2$;

$SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, $SO_2-(CH_2)_n$-phenyl, wherein n is 0–6 and the phenyl radical may be substituted up to two times by F, Cl, Br, OH, $CF_3$, $NO_2$, CN, $OCF_3$, $O-(C_1-C_6)$-alkyl, $(C_1-C_6)$-alkyl or $NH_2$;

$NH_2$, $NH-(C_1-C_6)$-alkyl, $N[(C_1-C_6)$-alkyl$]_2$, $NH-(CO)-(C_1-C_7)$alkyl, phenyl, biphenylyl, $O-(CH_2)_n$-phenyl, where n is 0–6, 1- or 2-naphthyl, 2-, 3- or 4-pyridyl, 2- or 3-furanyl or 2- or 3-thienyl, wherein any of the phenyl, biphenyl, naphthyl, pyridyl, furanyl or thienyl rings may be substituted one to three times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N[(C_1-C_6)$-alkyl$]_2$, $SO_2-CH_3$, COOH, $COO-(C_1-C_6)$-alkyl or $CONH_2$;

1,2,3-triazol-5-yl, wherein the triazole ring may be substituted in the 1-, 2- or 3-position by methyl or benzyl; or tetrazol-5-yl, where the tetrazole ring may be substituted in the 1- or 2 position by methyl or benzyl;

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, $C(O)-(C_1-C_6)$-alkyl, $C(O)-(C_3-C_6)$-cycloalkyl, $C(O)-(CH_2)_n$-phenyl, $C(O)-(CH_2)_n$-thienyl, $C(O)-(CH_2)_n$-pyridyl or $C(O)-(CH_2)_n$-furyl, wherein n is 0–5 and in which any of phenyl, thienyl, pyridyl or furyl may be substituted up to two times by Cl, F, CN, $CF_3$, $(C_1-C_3)$-alkyl, OH or $O-(C_1-C_6)$-alkyl;

R3 is H, $(C_1-C_6)$-alkyl, F, CN, $N_3$, $O-(C_1-C_6)$-alkyl, $(CH_2)_n$-phenyl, $(CH_2)_n$-thienyl, $(CH_2)_n$-pyridyl $(CH_2)_n$-furyl, where n is 0–5 and in which phenyl, thienyl, pyridyl or furyl may be substituted up to two times by Cl, F, CN, $CF_3$, $(C_1-C_3)$-alkyl, OH or $O-(C_1-C_6)$-alkyl; $OC(O)CH_3$, $(C_2-C_6)$-alkynyl, $(C_2-C_6)$-alkenyl, $COO(C_1-C_6)$-alkyl, $C(O)OH$, $C(O)NH_2$, $C(O)NHCH_3$ or $C(O)N(CH_3)_2$;

R4 is $(CH_2)_n-R5$, wherein n is 0–6;

R5 is phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl;

and R5 is substituted by $NH-SO_2-(C_1-C_6)$-alkyl or $NH-SO_2$-phenyl, wherein the phenyl ring may be substituted up to two times by F, Cl, CN, OH, $(C_1-C_6)$-alkyl, $O-(C_1-C_6)$-alkyl, $CF_3$, COOH, $COO(C_1-C_6)$-alkyl, $CONH_2$, $(CH_2)_n-SO_2-(C_1-C_6)$-alkyl, wherein n is 1–6, $(CH_2)_m-SO_2-NH_2$, $(CH_2)_m-SO_2-NH-(C_1-C_6)$-alkyl, $(CH_2)_m-SO_2-N[(C_1-C_6)$-alkyl$]_2$ or $(CH_2)_m-SO_2-N(=CH-N(CH_3)_2)$, wherein m is 0–6;

and R5 may be further substituted by F, Cl, Br, OH, $CF_3$, $NO_2$, CN, $OCF_3$, $O-(C_1-C_6)$-alkyl, $S-(C_1-C_6)$-alkyl, $SO-(C_1-C_6)$-alkyl, $(C_1-C_6)$-alkyl, $(C_3-C_6)$-cycloalkyl, COOH, $COO(C_1-C_6)$-alkyl, $COO(C_3-C_6)$-cycloalkyl, $CONH_2$, $CONH(C_1-C_6)$-alkyl, $CON[(C_1-C_6)$-alkyl$]_2$, $CONH(C_3-C_6)$-cycloalkyl, $NH_2$, $NH-CO-(C_1-C_6)$-alkyl, $NH-CO$-phenyl, pyrrolidin-1-yl, morpholin-1-yl, piperidin-1-yl, piperazin-1-yl, 4-methylpiperazin-1-yl, $(CH_2)_n$-phenyl, $O-(CH_2)_n$-phenyl, $S-(CH_2)_n$-phenyl, $SO_2-(CH_2)_n$-phenyl, wherein n is 0–3;

and its physiologically acceptable salts and physiologically functional derivatives and further comprising one or more anorectic active ingredients.

2. A pharmaceutical composition according to claim 1, wherein

R1, R' are independently selected from H, F, Cl, Br, I, $CF_3$, $NO_2$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $O-(C_1-C_6)$-alkyl, wherein one hydrogen of the alkyl radicals may be replaced by OH $OC(O)CH_3$, $OC(O)H$, $O-CH_2-Ph$, $NH_2$, $NH-CO-CH_3$ or $N(COOCH_2Ph)_2$;

$SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, $SO_2-(CH_2)_n$-phenyl, wherein n is 0–6 and the phenyl radical may be substituted up to two times by F, Cl, Br, OH, $CF_3$, $NO_2$, CN, $OCF_3$, $O-(C_1-C_6)$-alkyl, $(C_1-C_6)$-alkyl, $NH_2$;

$NH_2$, $NH-(C_1-C_6)$-alkyl, $N[(C_1-C_6)$-alkyl$]_2$, $NH-(CO)-(C_1-C_7)$alkyl, phenyl, biphenylyl, $O-(CH_2)_n$-phenyl, wherein n is 0–6, 1- or 2-naphthyl, 2-, 3- or 4-pyridyl, 2- or 3-furanyl or 2- or 3-thienyl where the phenyl, biphenylyl, naphthyl, pyridyl, furanyl or thienyl rings can in each case be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N[(C_1-C_6)$-alkyl$]_2$, $SO_2CH_3$, COOH, $COO-(C_1-C_6)$-alkyl, $CONH_2$; 1,2,3-triazol-5-yl, where the triazole ring can be substituted in the 1-, 2- or 3-position by methyl or benzyl; or tetrazol-5-yl, where the tetrazole ring can be substituted in the 1- or 2-position by methyl or benzyl;

R2 is H, $(C_1-C_6)$-alkyl, $(C_3-C_6)$-cycloalkyl, $(CH_2)_n$-phenyl, $(CH_2)_n$-thienyl, $CH_2)_n$-pyridyl, $(CH_2)_n$-furyl, $C(O)-(C_1-C_6)$-alkyl, $C(O)-(C_3-C_6)$-cycloalkyl, C(O)—(CH$_2$)$_n$-phenyl, C(O)—(CH$_2$)$_n$-thienyl, C(O)—(CH$_2$)$_n$-pyridyl or C(O)—(CH$_2$)$_n$-furyl,
  wherein n is 0–5 and in which phenyl, thienyl, pyridyl and furyl may be substituted up to two times by Cl, F, CN, CF$_3$, (C$_1$–C$_3$)-alkyl, OH, O—(C$_1$–C$_6$)-alkyl;

R3 is H, (C$_1$–C$_6$)-alkyl, F, CN, N$_3$, O—(C$_1$–C$_6$)-alkyl, (CH$_2$)$_n$-phenyl, (CH$_2$)-thienyl, (CH$_2$)$_n$-pyridyl, (CH$_2$)$_n$-furyl,
  wherein n is 0–5 and in which phenyl, thienyl, pyridyl and furyl can in each case be substituted up to two times by Cl, F, CN, CF$_3$, (C$_1$–C$_3$)-alkyl, OH, O—(C$_1$–C$_6$)-alkyl;
  OC(O)CH$_3$, (C$_2$–C$_6$)-alkynyl, (C$_2$–C$_6$)-alkenyl, COO (C$_1$–C$_6$)-alkyl, C(O)OH, C(O)NH$_2$, C(O)NHCH$_3$ or C(O)N(CH$_3$)$_2$;

R4 is (CH$_2$)$_n$—R5, wherein n is 0–6;

R5 is phenyl, biphenylyl, 1- or 2-naphthyl, 2-, 3- or 4-pyridyl or 2- or 3-thienyl;

and R5 is substituted by
  NH—SO$_2$—(C$_1$–C$_6$)-alkyl, NH—SO$_2$-phenyl,
  wherein the phenyl ring may be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl, CONH$_2$;
  (CH$_2$)$_n$—SO$_2$—(C$_1$–C$_6$)-alkyl, wherein n is 1–6,
  (CH$_2$)$_n$—SO$_2$—NH$_2$, (CH$_2$)$_m$—SO$_2$—NH—(C$_1$–C$_6$)-alkyl, (CH$_2$)$_m$—SO$_2$—N[(C$_1$–C$_6$]-alkyl)$_2$ or (CH$_2$)$_n$—SO$_2$—N(=CH—N(CH$_3$)$_2$), wherein m is 0–6;

and R5 may be further substituted by F, Cl, Br, OH, CF$_3$, CN, OCF$_3$, O—(C$_1$–C$_6$)-alkyl, (C$_1$–C$_6$)-alkyl, (C$_3$–C$_6$)-cycloalkyl, COOH, COO(C$_1$–C$_6$)-alkyl, COO (C$_3$–C$_6$)-cycloalkyl, CONH$_2$, CONH(C$_1$–C$_6$)-alkyl, CON[(C$_1$–C$_6$)-alkyl]$_2$, NH$_2$, NH—CO—(C$_1$–C$_6$)-alkyl, NH—CO-phenyl, (CH$_2$)$_n$-phenyl, O—(CH$_2$)$_n$-phenyl, S—(CH$_2$)$_n$-phenyl, SO$_2$—(CH$_2$)$_n$-phenyl, wherein n is 0–3;

and their physiologically acceptable salts and physiologically functional derivatives.

3. A pharmaceutical composition according to claim 2, wherein

R1, R' are independently selected from H, F, Cl, Br, I, CF$_3$, NO$_2$, CN, COOH, COO(C$_1$–C$_6$)-alkyl, CONH$_2$, (C$_1$–C$_6$)-alkyl, (C$_2$–C$_6$)-alkenyl, (C$_2$–C$_6$)-alkynyl, O—(C$_1$–C$_6$)-alkyl, SO$_2$—NH$_2$, phenyl, O—(CH$_2$)$_n$-phenyl,
  wherein n is 0–6, wherein the phenyl rings can in each case be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, CONH$_2$;

R2 is H, (C$_1$–C$_6$)-alkyl, (C$_3$–C$_6$)-cycloalkyl, (CH$_2$)$_n$-phenyl, C(O)—(C$_1$–C$_6$)-alkyl or C(O)—(CH$_2$)$_n$-phenyl,
  wherein n is 0–5 and in which phenyl can be substituted up to two times by Cl, F, CN, CF$_3$, (C$_1$–C$_3$)-alkyl, OH, O—(C$_1$–C$_6$)-alkyl;

R3S is H, (C$_1$–C$_6$)-alkyl, F, (CH$_2$)$_n$-phenyl,
  wherein n is 0–5 and in which phenyl can be substituted up to two times by Cl, F, CN, CF$_3$, (C$_1$–C$_3$)-alkyl, OH, O—(C$_1$–C$_6$)-alkyl; COO(C$_1$–C$_6$)-alkyl, C(O)OH or C(O)NH$_2$;

R4 is (CH$_2$)$_n$—R5, wherein n is 0–6; or

R5 is phenyl, 1- or 2-naphthyl;

and R5 is substituted by
  NH—SO$_2$—(C$_1$–C$_6$)-alkyl, NH—SO$_2$-phenyl,
  wherein the phenyl ring can be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl, CONH$_2$;
  (CH$_2$)$_n$—SO$_2$—(C$_1$–C$_6$)-alkyl, wherein n is 1–6,
  (CH$_2$)$_m$—SO$_2$—NH$_2$, (CH$_2$)$_m$—SO$_2$—NH(C$_1$–C$_6$)-alkyl, (CH$_2$)$_m$—SO$_2$—N[(C$_1$–C$_6$)-alkyl]$_2$ or (CH$_2$)$_m$—SO2—N(=CH—N(CH3)2), wherein m is 0–6;

R5 may further be substituted by F, Cl, Br, OH, CF$_3$, CN, OCF$_3$, O—(C$_1$–C$_6$)-alkyl, (C$_1$–C$_6$)-alkyl, COOH, COO(C$_1$–C$_6$)-alkyl, CONH$_2$, NH$_2$, NH—CO—(C$_1$–C$_6$)-alkyl, NH—CO-phenyl, (CH$_2$)$_n$-phenyl, O—(CH$_2$)$_n$-phenyl, SO$_2$—(CH$_2$)$_n$-phenyl, wherein n is 0–3;

and their physiologically acceptable salts.

4. A method for the prophylaxis or treatment of obesity comprising administering to a patient in need thereof one or more compounds of formula I:

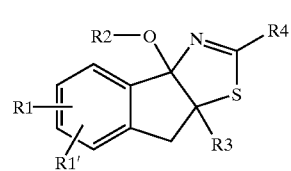

in which

R1, R1' are independently selected from H, F, Cl, Br, I, CF$_3$, NO$_2$, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O—(C$_1$–C$_6$)-alkyl,
  wherein one or more of the hydrogens of the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$;
  SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl,
  wherein n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$;
  NH$_2$, NH—(C$_1$–C$_6$)-alkyl, N[(C$_1$–C$_6$)-alkyl]$_2$, NH—(CO)—(C$_1$–C$_7$)alkyl, phenyl, biphenylyl, O—(CH$_2$)$_n$-phenyl, where n is 0–6, 1- or 2-naphthyl, 2-, 3- or 4-pyridyl, 2- or 3-furanyl or 2- or 3-thienyl,
  wherein any of the phenyl, biphenyl, naphthyl, pyridyl, furanyl or thienyl rings may be substituted one to three times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N[(C$_1$–C$_6$)-alkyl]$_2$, SO$_2$—CH$_3$, COOH, COO—(C$_1$–C$_6$)-alkyl or CONH$_2$;
  1,2,3-triazol-5-yl, wherein the triazole ring may be substituted in the 1-, 2- or 3-position by methyl or benzyl; or tetrazol-5-yl, where the tetrazole ring may be substituted in the 1- or 2 position by methyl or benzyl;

R2 is H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl or C(O)—(CH$_2$)$_n$-furyl,
  wherein n is 0–5 and in which any of phenyl, thienyl, pyridyl or furyl may be substituted up to two times by Cl, F, CN, $CF_3$, $(C_1-C_3)$-alkyl, OH or O—$(C_1-C_6)$-alkyl;

R3 is H, $(C_1-C_6)$-alkyl, F, CN, $N_3$, O—$(C_1-C_6)$-alkyl, $(CH_2)_n$-phenyl, $(CH_2)_n$-thienyl, $(CH_2)_n$-pyridyl $(CH_2)_n$-furyl,
where n is 0–5 and in which phenyl, thienyl, pyridyl or furyl may be substituted up to two times by Cl, F, CN, $CF_3$, $(C_1-C_3)$-alkyl, OH or O—$(C_1-C_6)$-alkyl;
$OC(O)CH_3$, $(C_2-C_6)$-alkynyl, $(C_2-C_6)$-alkenyl, COO $(C_1-C_6)$-alkyl, C(O)OH, $C(O)NH_2$, $C(O)NHCH_3$ or $C(O)N(CH_3)_2$;

R4 is $(CH_2)_n$—R5, wherein n is 0–6;

R5 is phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl;

and R5 is substituted by

NH—$SO_2$—$(C_1-C_6)$-alkyl or NH—$SO_2$-phenyl,
wherein the phenyl ring may be substituted up to two times by F, Cl, CN, OH, $(C_1-C_6)$-alkyl, O—$(C_1-C_6)$-alkyl, $CF_3$, COOH, $COO(C_1-C_6)$-alkyl, $CONH_2$, $(CH_2)_n$—$SO_2$—$(C_1-C_6)$-alkyl, wherein n is 1–6, $(CH_2)_m$—$SO_2$—$NH_2$, $(CH_2)_m$—$SO_2$—NH—$(C_1-C_6)$-alkyl, $(CH_2)_m$—$SO_2$—N$[(C_1-C_6)$-alkyl$]_2$ or $(CH_2)_m$—$SO_2$—N(=CH—N$(CH_3)_2)$, wherein m is 0–6;

and R5 may be further substituted by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $(C_1-C_6)$-alkyl, $(C_3-C_6)$-cycloalkyl, COOH, $COO(C_1-C_6)$-alkyl, $COO(C_3-C_6)$-cycloalkyl, $CONH_2$, $CONH(C_1-C_6)$-alkyl, CON$[(C_1-C_6)$-alkyl$]_2$, $CONH(C_3-C_6)$-cycloalkyl, $NH_2$, NH—CO—$(C_1-C_6)$-alkyl, NH—CO-phenyl, pyrrolidin-1-yl, morpholin-1-yl, piperidin-1-yl, piperazin-1-yl, 4-methylpiperazin-1-yl, $(CH_2)_n$-phenyl, O—$(CH_2)_n$-phenyl, S—$(CH_2)_n$-phenyl, $SO_2$—$(CH_2)_n$-phenyl, wherein n is 0–3;

and its physiologically acceptable salts and physiologically functional derivatives further comprising administering an additional anorectic active agent.

5. The method of claim 4, wherein

R1, R' are independently selected from H, F, Cl, Br, I, $CF_3$, $NO_2$, CN, COOH, $COO(C_1-C_6)$-alkyl, $CONH_2$, $CONH(C_1-C_6)$-alkyl, CON$[(C_1-C_6)$-alkyl$]_2$, $(C_1-C_6)$-alkyl, $(C_2-C_6)$-alkenyl, $(C_2-C_6)$-alkynyl, O—$(C_1-C_6)$-alkyl,
wherein one hydrogen of the alkyl radicals may be replaced by OH, $OC(O)CH_3$, OC(O)H, O—$CH_2$—Ph, $NH_2$, NH—CO—$CH_3$ or $N(COOCH_2Ph)_2$;
$SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl, $SO_2$—$(CH_2)_n$-phenyl,
wherein n is 0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl, $NH_2$;
$NH_2$, NH—$(C_1-C_6)$-alkyl, $N[(C_1-C_6)$-alkyl$]_2$, NH—(CO)—$(C_1-C_7)$alkyl, phenyl, biphenylyl, O—$(CH_2)_n$-phenyl, wherein n is 0–6, 1- or 2-naphthyl, 2-, 3- or 4-pyridyl, 2- or 3-furanyl or 2- or 3-thienyl where the phenyl, biphenylyl, naphthyl, pyridyl, furanyl or thienyl rings can in each case be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N$[(C_1-C_6)$-alkyl$]_2$, $SO_2CH_3$, COOH, COO—$(C_1-C_6)$-alkyl, $CONH_2$; 1,2,3-triazol-5-yl, where the triazole ring can be substituted in the 1-, 2- or 3-position by methyl or benzyl; or tetrazol-5-yl, where the tetrazole ring can be substituted in the 1- or 2-position by methyl or benzyl;

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, C(O)—$(C_1-C_6)$-alkyl, C(O)—$(C_3-C_6)$-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl,
wherein n is 0–5 and in which phenyl, thienyl, pyridyl and furyl may be substituted up to two times by Cl, F, CN, $CF_3$, $(C_1-C_3)$-alkyl, OH, O—$(C_1-C_6)$-alkyl;

R3 is H, $(C_1-C_6)$-alkyl, F, CN, $N_3$, O—$(C_1-C_6)$-alkyl, $(CH_2)_n$-phenyl, $(CH_2)$-thienyl, $(CH_2)_n$-pyridyl, $(CH_2)_n$-furyl,
wherein n is 0–5 and in which phenyl, thienyl, pyridyl and furyl can in each case be substituted up to two times by Cl, F, CN, $CF_3$, $(C_1-C_3)$-alkyl, OH, O—$(C_1-C_6)$-alkyl;
$OC(O)CH_3$, $(C_2-C_6)$-alkynyl, $(C_2-C_6)$-alkenyl, COO $(C_1-C_6)$-alkyl, C(O)OH, $C(O)NH_2$, $C(O)NHCH_3$ or $C(O)N(CH_3)_2$;

R4 is $(CH_2)_n$—R5, wherein n is 0–6;

R5 is phenyl, biphenylyl, 1- or 2-naphthyl, 2-, 3- or 4-pyridyl or 2- or 3-thienyl;

and R5 is substituted by

NH—$SO_2$—$(C_1-C_6)$-alkyl, NH—$SO_2$-phenyl,
wherein the phenyl ring may be substituted up to two times by F, Cl, CN, OH, $(C_1-C_6)$-alkyl, O—$(C_1-C_6)$-alkyl, $CF_3$, COOH, $COO(C_1-C_6)$-alkyl, $CONH_2$;
$(CH_2)_n$—$SO_2$—$(C_1-C_6)$-alkyl, wherein n is 1–6, $(CH_2)_n$—$SO_2$—$NH_2$, $(CH_2)_m$—$SO_2NH$—$(C_1-C_6)$-alkyl, $(CH_2)_m$—$SO_2N[(C_1-C_6)$-alkyl$]_2$ or $(CH_2)_n$—$SO_2$—N(=CH—$N(CH_3)_2)$, wherein m is 0–6;

and R5 may be further substituted by F, Cl, Br, OH, $CF_3$, CN, $OCF_3$, O—$(C_1-C_6)$-alkyl, $(C_1-C_6)$-alkyl, $(C_3-C_6)$-cycloalkyl, COOH, $COO(C_1-C_6)$-alkyl, COO $(C_3-C_6)$-cycloalkyl, $CONH_2$, $CONH(C_1-C_6)$-alkyl, CON$[(C_1-C_6)$-alkyl$]_2$, $NH_2$, NH—CO—$(C_1-C_6)$-alkyl, NH—CO-phenyl, $(CH_2)_n$-phenyl, O—$(CH_2)_n$-phenyl, S—$(CH_2)_n$-phenyl, $SO_2$—$(CH_2)_n$-phenyl, wherein n is 0–3;

and their physiologically acceptable salts and physiologically functional derivatives.

6. The method of claim 4 wherein

R1, R' are independently selected from H, F, Cl, Br, I, $CF_3$, $NO_2$, CN, COOH, $COO(C_1-C_6)$-alkyl, $CONH_2$, $(C_1-C_6)$-alkyl, $(C_2-C_6)$-alkenyl, $(C_2-C_6)$-alkynyl, O—$(C_1-C_6)$-alkyl, $SO_2$—$NH_2$, phenyl, O—$(CH_2)_n$-phenyl,
wherein n is 0–6, wherein the phenyl rings can in each case be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $CONH_2$;

R2 is H, $(C_1-C_6)$-alkyl, $(C_3-C_6)$-cycloalkyl, $(CH_2)_n$-phenyl, C(O)—$(C_1-C_6)$-alkyl or C(O)—$(CH_2)_n$-phenyl, wherein n is 0–5 and in which phenyl can be substituted up to two times by Cl, F, CN, CF$_3$, (C$_1$–C$_3$)-alkyl, OH, O—(C$_1$–C$_6$)-alkyl;

R3 is H, (C$_1$–C$_6$)-alkyl, F, (CH$_2$)$_n$-phenyl,
wherein n is 0–5 and in which phenyl can be substituted up to two times by Cl, F, CN, CF$_3$, (C$_1$–C$_3$)-alkyl, OH, O—(C$_1$–C$_6$)-alkyl; COO(C$_1$–C$_6$)-alkyl, C(O)OH or C(O)NH$_2$;

R4 is (CH$_2$)$_n$—R5, wherein n is 0–6; or

R5 is phenyl, 1- or 2-naphthyl;

and R5 is substituted by
NH—SO$_2$—(C$_1$–C$_6$)-alkyl, NH—SO$_2$-phenyl,
wherein the phenyl ring can be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl, CONH$_2$;

(CH$_2$)$_n$—SO$_2$—(C$_1$–C$_6$)-alkyl, wherein n is 1–6,
(CH$_2$)$_m$—SO$_2$—NH$_2$, (CH$_2$)$_m$—SO$_2$—NH—(C$_{1-C6}$)-alkyl, (CH$_2$)$_m$—SO$_2$—N[(C$_1$–C$_6$)-alkyl]$_2$ or (CH2)$_m$—SO2—N(=CH—N(CH3)2), wherein m is 0–6;

and R5 may further be substituted by F, Cl, Br, OH, CF$_3$, CN, OCF$_3$, O—(C$_1$–C$_6$)-alkyl, (C$_1$–C$_6$)-alkyl, COOH, COO(C$_1$–C$_6$)-alkyl, CONH$_2$, NH$_2$, NH—CO—(C$_1$–C$_6$)-alkyl, NH—CO-phenyl, (CH$_2$)$_n$-phenyl, O—(CH$_2$)$_n$-phenyl, SO$_2$—(CH$_2$)$_n$-phenyl, wherein n is 0–3;

and their physiologically acceptable salts.

7. A method for the prophylaxis or treatment of type II diabetes comprising administering to a patient in need thereof one or more compounds of formula I:

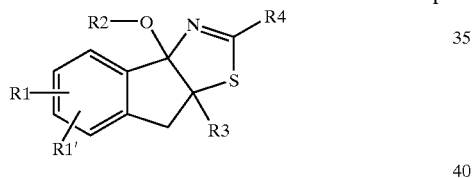

in which
R1, R1' are independently selected from H, F, Cl, Br, I, CF$_3$, NO$_2$, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O—(C$_1$–C$_6$)-alkyl,
wherein one or more of the hydrogens of the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$;

SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl,
wherein n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$;

NH$_2$, NH—(C$_1$–C$_6$)-alkyl, N[(C$_1$–C$_6$)-alkyl]$_2$, NH—(CO)—(C$_1$–C$_7$)alkyl, phenyl, biphenylyl, O—(CH$_2$)$_n$-phenyl, where n is 0–6, 1- or 2-naphthyl, 2-, 3- or 4-pyridyl, 2- or 3-furanyl or 2- or 3-thienyl,
wherein any of the phenyl, biphenyl, naphthyl, pyridyl, furanyl or thienyl rings may be substituted one to three times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N[(C$_1$–C$_6$)-alkyl]$_2$, SO$_2$—CH$_3$, COOH, COO—(C$_1$–C$_6$)-alkyl or CONH$_2$;

1,2,3-triazol-5-yl, wherein the triazole ring may be substituted in the 1-, 2- or 3-position by methyl or benzyl; or tetrazol-5-yl, where the tetrazole ring may be substituted in the 1- or 2 position by methyl or benzyl;

R2 is H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl or C(O)—(CH$_2$)$_n$-furyl,
wherein n is 0–5 and in which any of phenyl, thienyl, pyridyl or furyl may be substituted up to two times by Cl, F, CN, CF$_3$, (C$_1$–C$_3$)-alkyl, OH or O—(C$_1$–C$_6$)-alkyl;

R3 is H, (C$_1$–C$_6$)-alkyl, F, CN, N$_3$, O—(C$_1$–C$_6$)-alkyl, (CH$_2$)$_n$-phenyl, (CH$_2$)$_n$-thienyl, (CH$_2$)$_n$-pyridyl (CH$_2$)$_n$-furyl,
where n is 0–5 and in which phenyl, thienyl, pyridyl or furyl may be substituted up to two times by Cl, F, CN, CF$_3$, (C$_1$–C$_3$)-alkyl, OH or O—(C$_1$–C$_6$)-alkyl; OC(O)CH$_3$, (C$_2$–C$_6$)-alkynyl, (C$_2$–C$_6$)-alkenyl, COO(C$_1$–C$_6$)-alkyl, C(O)OH, C(O)NH$_2$, C(O)NHCH$_3$ or C(O)N(CH$_3$)$_2$;

R4 is (CH$_2$)$_n$—R5, wherein n is 0–6;

R5 is phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl;

and R5 is substituted by
NH—SO$_2$—(C$_1$–C$_6$)-alkyl or NH—SO$_2$-phenyl,
wherein the phenyl ring may be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl, CONH$_2$, (CH$_2$)$_n$—SO$_2$—(C$_1$–C$_6$)-alkyl, wherein n is 1–6, (CH$_2$)$_m$—SO$_2$—NH$_2$, (CH$_2$)$_m$—SO$_2$—NH—(C$_1$–C$_6$)-alkyl, (CH$_2$)$_m$—SO$_2$—N[(C$_1$–C$_6$)-alkyl]$_2$ or (CH$_2$)$_m$—SO$_2$—N(=CH—N(CH$_3$)$_2$), wherein m is 0–6;

and R5 may be further substituted by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, (C$_1$–C$_6$)-alkyl, (C$_3$–C$_6$)-cycloalkyl, COOH, COO(C$_1$–C$_6$)-alkyl, COO(C$_3$–C$_6$)-cycloalkyl, CONH$_2$, CONH(C$_1$–C$_6$)-alkyl, CON[(C$_1$–C$_6$)-alkyl]$_2$, CONH(C$_3$–C$_6$)-cycloalkyl, NH$_2$, NH—CO—(C$_1$–C$_6$)-alkyl, NH—CO-phenyl, pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl, SO$_2$—(CH$_2$)$_n$-phenyl, wherein n is 0–3;

and its physiologically acceptable salts and physiologically functional derivatives,
further comprising administering an additional anorectic agent.

8. The method of claim 7 wherein
R1, R' are independently selected from H, F, Cl, Br, I, CF$_3$, NO$_2$, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O—(C$_1$–C$_6$)-alkyl, wherein one hydrogen of the alkyl radicals may be replaced by OH, OC(O)CH$_3$, OC(O)H, O—CH$_2$—Ph, NH$_2$, NH—CO—CH$_3$ or N(COOCH$_2$Ph)$_2$;

SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl, wherein n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl, NH$_2$;

NH$_2$, NH—(C$_1$–C$_6$)-alkyl, N[(C$_1$–C$_6$)-alkyl]$_2$, NH—(CO)—(C$_1$–C$_7$)alkyl, phenyl, biphenylyl, O—(CH$_2$)$_n$-phenyl, wherein n is 0–6, 1- or 2-naphthyl, 2-, 3- or 4-pyridyl, 2- or 3-furanyl or 2- or 3-thienyl where the phenyl, biphenyl, naphthyl, pyridyl, furanyl or thienyl rings can in each case be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N[(C$_1$–C$_6$)-alkyl]$_2$, SO$_2$CH$_3$, COOH, COO—(C$_1$–C$_6$)-alkyl, CONH$_2$; 1,2,3-triazol-5-yl, where the triazole ring can be substituted in the 1-, 2- or 3-position by methyl or benzyl; or tetrazol-5-yl, where the tetrazole ring can be substituted in the 1- or 2-position by methyl or benzyl;

R2 is H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl or C(O)—(CH$_2$)$_n$-furyl, wherein n is 0–5 and in which phenyl, thienyl, pyridyl and furyl may be substituted up to two times by Cl, F, CN, CF$_3$, (C$_1$–C$_3$)-alkyl, OH, O—(C$_1$–C$_6$)-alkyl;

R3 is H, (C$_1$–C$_6$)-alkyl, F, CN, N$_3$, O—(C$_1$–C$_6$)-alkyl, (CH$_2$)$_n$-phenyl, (CH$_2$)-thienyl, (CH$_2$)$_n$-pyridyl, (CH$_2$)$_n$-furyl, wherein n is 0–5 and in which phenyl, thienyl, pyridyl and furyl can in each case be substituted up to two times by Cl, F, CN, CF$_3$, (C$_1$–C$_3$)-alkyl, OH, O—(C$_1$–C$_6$)-alkyl;

OC(O)CH$_3$, (C$_2$C$_6$)-alkynyl, (C$_2$–C$_6$)-alkenyl, COO(C$_1$–C$_6$)-alkyl, C(O)OH, C(O)NH$_2$, C(O)NHCH$_3$ or C(O)N(CH$_3$)$_2$;

R4 is (CH$_2$)$_n$—R5, wherein n is 0–6;

R5 is phenyl, biphenylyl, 1- or 2-naphthyl, 2-, 3- or 4-pyridyl or 2- or 3-thienyl;

and R5 is substituted by

NH—SO$_2$—(C$_1$–C$_6$)-alkyl, NH—SO$_2$-phenyl, wherein the phenyl ring may be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl, CONH$_2$;

(CH$_2$)$_n$—SO$_2$—(C$_1$–C$_6$)-alkyl, wherein n is 1–6, (CH$_2$)$_n$—SO$_2$—NH$_2$, (CH$_2$)$_m$—SO$_2$—NH—(C$_1$–C$_6$)-alkyl, (CH$_2$)$_m$—SO$_2$—N[(C$_1$–C$_6$]-alkyl)$_2$ or (CH$_2$)$_n$—SO$_2$—N(=CH—N(CH$_3$)$_2$), wherein m is 0–6;

and R5 may be further substituted by F, Cl, Br, OH, CF$_3$, CN, OCF$_3$, O—(C$_1$–C$_6$)-alkyl, (C$_1$–C$_6$)-alkyl, (C$_3$–C$_6$)-cycloalkyl, COOH, COO(C$_1$–C$_6$)-alkyl, COO(C$_3$–C$_6$)-cycloalkyl, CONH$_2$, CONH(C$_1$–C$_6$)-alkyl, CON[(C$_1$–C$_6$)-alkyl]$_2$, NH$_2$, NH—CO—(C$_1$–C$_6$)-alkyl, NH—CO-phenyl, (CH$_2$)$_n$-phenyl, O—(CH$_2$)$_n$-phenyl, S—(CH$_2$)$_n$-phenyl, SO$_2$—(CH$_2$)$_n$-phenyl, wherein n is 0–3;

and their physiologically acceptable salts and physiologically functional derivatives.

9. The method of claim 7 wherein

R1, R' are independently selected from H, F, Cl, Br, I, CF$_3$, NO$_2$, CN, COOH, COO(C$_1$–C$_6$)-alkyl, CONH$_2$, (C$_1$–C$_6$)-alkyl, (C$_2$–C$_6$)-alkenyl, (C$_2$–C$_6$)-alkynyl, O—(C$_1$–C$_6$)-alkyl, SO$_2$—NH$_2$, phenyl, O—(CH$_2$)$_n$-phenyl, wherein n is 0–6, wherein the phenyl rings can in each case be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, CONH$_2$;

R2 is H, (C$_1$–C$_6$)-alkyl, (C$_3$–C$_6$)-cycloalkyl, (CH$_2$)$_n$-phenyl, C(O)—(C$_1$–C$_6$)-alkyl or C(O)—(CH$_2$)$_n$-phenyl, wherein n is 0–5 and in which phenyl can be substituted up to two times by Cl, F, CN, CF$_3$, (C$_1$–C$_3$)-alkyl, OH, O—(C$_1$–C$_6$)-alkyl;

R3 is H, (C$_1$–C$_6$)-alkyl, F, (CH$_2$)$_n$-phenyl, wherein n is 0–5 and in which phenyl can be substituted up to two times by Cl, F, CN, CF$_3$, (C$_1$–C$_3$)-alkyl, OH, O—(C$_1$–C$_6$)-alkyl; COO(C$_1$–C$_6$)-alkyl, C(O)OH or C(O)NH$_2$;

R4 is (CH$_2$)$_n$—R5, wherein n is 0–6; or

R5 is phenyl, 1- or 2-naphthyl;

and R5 is substituted by

NH—SO$_2$—(C$_1$–C$_6$)-alkyl, NH—SO$_2$-phenyl, wherein the phenyl ring can be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl, CONH$_2$;

(CH$_2$)$_n$—SO$_2$—(C$_1$–C$_6$)-alkyl, wherein n is 1–6, (CH$_2$)$_m$—SO$_2$NH$_2$, (CH$_2$)$_m$—SO$_2$—NH—(C$_1$–C$_6$)-alkyl, (CH$_2$)$_m$—SO$_2$—N[(C$_1$–C$_6$)-alkyl]$_2$ or (CH2)$_m$—SO2—N(=CH—N(CH3)2), wherein m is 0–6;

and R5 may further be substituted by F, Cl, Br, OH, CF$_3$, CN, OCF$_3$, O—(C$_1$–C$_6$)-alkyl, (C$_1$–C$_6$)-alkyl, COOH, COO(C$_1$–C$_6$)-alkyl, CONH$_2$, NH$_2$, NH—CO—(C$_1$–C$_6$)-alkyl, NH—CO-phenyl, (CH$_2$)$_n$-phenyl, O—(CH$_2$)$_n$-phenyl, SO$_2$—(CH$_2$)$_n$-phenyl, wherein n is 0–3;

and their physiologically acceptable salts.

10. A method for enhancing lipid metabolism comprising administering to a patient in need thereof one or more compounds of formula I:

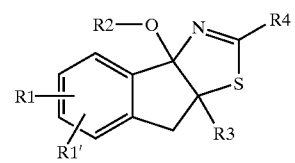

in which

R1, R' are independently selected from H, F, Cl, Br, I, CF$_3$, NO$_2$, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O—(C$_1$–C$_6$)-alkyl, wherein one or more of the hydrogens of the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$;

SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—

($C_1$–$C_6$)-alkyl, SO—$(CH_2)_n$-phenyl, $SO_2$-($C_1$–$C_6$)-alkyl, $SO_2$—$(CH_2)_n$-phenyl,
wherein n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$;

$NH_2$, NH—($C_1$–$C_6$)-alkyl, N[($C_1$–$C_6$)-alkyl]$_2$, NH—(CO)—($C_1$–$C_7$)alkyl, phenyl, biphenylyl, O—$(CH_2)_n$-phenyl, where n is 0–6, 1- or 2-naphthyl, 2-, 3- or 4-pyridyl, 2- or 3-furanyl or 2- or 3-thienyl,
wherein any of the phenyl, biphenyl, naphthyl, pyridyl, furanyl or thienyl rings may be substituted one to three times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N[($C_1$–$C_6$)-alkyl]$_2$, $SO_2$—$CH_3$, COOH, COO—($C_1$–$C_6$)-alkyl or $CONH_2$;

1,2,3-triazol-5-yl, wherein the triazole ring may be substituted in the 1-, 2- or 3-position by methyl or benzyl; or tetrazol-5-yl, where the tetrazole ring may be substituted in the 1- or 2 position by methyl or benzyl;

R2 is H, ($C_1$–$C_6$)-alkyl, ($C_3$–$C_6$)-cycloalkyl, $(CH_2)_n$-phenyl, $(CH_2)_n$-thienyl, $(CH_2)_n$-pyridyl, $(CH_2)_n$-furyl, C(O)—($C_1$–$C_6$)-alkyl, C(O)—($C_3$–$C_6$)cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl,
wherein n is 0–5 and in which any of phenyl, thienyl, pyridyl or furyl may be substituted up to two times by Cl, F, CN, $CF_3$, ($C_1$–$C_3$)-alkyl, OH or O—($C_1$–$C_6$)-alkyl;

R3 is H, ($C_1$–$C_6$)-alkyl, F, CN, $N_3$, O—($C_1$–$C_6$)-alkyl, $(CH_2)_n$-phenyl, $(CH_2)_n$-thienyl, $(CH_2)_n$-pyridyl $(CH_2)_n$-furyl,
where n is 0–5 and in which phenyl, thienyl, pyridyl or furyl may be substituted up to two times by Cl, F, CN, $CF_3$, ($C_1$–$C_3$)-alkyl, OH or O—($C_1$–$C_6$)-alkyl;
OC(O)$CH_3$, ($C_2$–$C_6$)-alkynyl, ($C_2$–$C_6$)-alkenyl, COO($C_1$–$C_6$)-alkyl, C(O)OH, C(O)$NH_2$, C(O)$NHCH_3$ or C(O)N($CH_3$)$_2$;

R4 is $(CH_2)_n$—R5, wherein n is 0–6;

R5 is phenyl, biphenylyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl;

and R5 is substituted by
NH—$SO_2$—($C_1$–$C_6$)-alkyl or NH—$SO_2$-phenyl,
wherein the phenyl ring may be substituted up to two times by F, Cl , CN, OH, ($C_1$–$C_6$)-alkyl, O—($C_1$–$C_6$)-alkyl, $CF_3$, COOH, COO($C_1$–$C_6$)-alkyl, $CONH_2$, $(CH_2)_n$—$SO_2$—($C_1$–$C_6$)-alkyl, wherein n is 1–6, $(CH_2)_m$—$SO_2$—$NH_2$, $(CH_2)_m$—$SO_2$—NH—($C_1$–$C_6$)-alkyl, $(CH_2)_m$—$SO_2$—N[($C_1$–$C_6$)-alkyl]$_2$ or $(CH_2)_m$—$SO_2$—N(=CH—N($CH_3$)$_2$), wherein m is 0–6;

and R5 may be further substituted by F, Cl, Br, OH, $CF_3$, $NO_2$, CN, $OCF_3$, O—($C_1$–$C_6$)-alkyl, S—($C_1$–$C_6$)-alkyl, SO—($C_1$–$C_6$)-alkyl, ($C_1$–$C_6$)-alkyl, ($C_3$–$C_6$)-cycloalkyl, COOH, COO($C_1$–$C_6$)-alkyl, COO($C_3$–$C_6$)-cycloalkyl, $CONH_2$, CONH($C_1$–$C_6$)-alkyl, CON[($C_1$–$C_6$)-alkyl]$_2$, CONH($C_3$–$C_6$)-cycloalkyl, $NH_2$, NH—CO—($C_1$–$C_6$)-alkyl, NH—CO-phenyl, pyrrolidin-1-yl, morpholin-1-yl, piperidin-1-yl, piperazin-1-yl, 4-methylpiperazin-1-yl, $(CH_2)_n$-phenyl, O—$(CH_2)_n$-phenyl, S—$(CH_2)_n$-phenyl, $SO_2$—$(CH_2)_n$-phenyl, wherein n is 0–3;

and its physiologically acceptable salts and physiologically functional derivatives
further comprising administering an additional anorectic active agent.

11. The method of claim 10 wherein
R1, R' are independently selected from H, F, Cl, Br, I, $CF_3$, $NO_2$, CN, COOH, COO($C_1$–$C_6$)-alkyl, $CONH_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl, O—($C_1$–$C_6$)-alkyl,
wherein one hydrogen of the alkyl radicals may be replaced by OH, OC(O)$CH_3$, OC(O)H, O—$CH_2$—Ph, $NH_2$, NH—CO—$CH_3$ or N(COOCH$_2$Ph)$_2$;

$SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—$(CH_2)_n$-phenyl, SO—($C_1$–$C_6$)-alkyl, SO—$(CH_2)_n$-phenyl, $SO_2$—($C_1$–$C_6$)-alkyl, $SO_2$($CH_2)_n$-phenyl,
wherein n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl, $NH_2$;

$NH_2$, NH—($C_1$–$C_6$)-alkyl, N[($C_1$–$C_6$)-alkyl]$_2$, NH—(CO)—($C_1$–$C_7$)alkyl, phenyl, biphenylyl, O—$(CH_2)_n$-phenyl, wherein n is 0–6, 1- or 2-naphthyl, 2-, 3- or 4-pyridyl, 2- or 3-furanyl or 2- or 3-thienyl where the phenyl, biphenylyl, naphthyl, pyridyl, furanyl or thienyl rings can in each case be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N[($C_1$–$C_6$)-alkyl]$_2$, $SO_2CH_3$, COOH, COO—($C_1$–$C_6$)-alkyl, $CONH_2$; 1,2,3-triazol-5-yl, where the triazole ring can be substituted in the 1-, 2- or 3-position by methyl or benzyl; or tetrazol-5-yl, where the tetrazole ring can be substituted in the 1- or 2-position by methyl or benzyl;

R2 is H, ($C_1$–$C_6$)-alkyl, ($C_3$–$C_6$)-cycloalkyl, $(CH_2)_n$-phenyl, $(CH_2)_n$-thienyl, $(CH_2)_n$-pyridyl, $(CH_2)_n$-furyl, C(O)—($C_1$–$C_6$)-alkyl, C(O)—($C_3$–$C_6$)-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl,
wherein n is 0–5 and in which phenyl, thienyl, pyridyl and furyl may be substituted up to two times by Cl, F, CN, $CF_3$, ($C_1$–$C_3$)-alkyl, OH, O—($C_1$–$C_6$)-alkyl;

R3 is H, ($C_1$–$C_6$)-alkyl, F, CN, $N_3$, O—($C_1$–$C_6$)-alkyl, $(CH_2)_n$-phenyl, $(CH_2)$-thienyl, $(CH_2)_n$-pyridyl, $(CH_2)_n$-furyl,
wherein n is 0–5 and in which phenyl, thienyl, pyridyl and furyl can in each case be substituted up to two times by Cl, F, CN, $CF_3$, ($C_1$–$C_3$)-alkyl, OH, O—($C_1$–$C_6$)-alkyl;

OC(O)$CH_3$, ($C_2$–$C_6$)-alkynyl, ($C_2$–$C_6$)-alkenyl, COO($C_1$–$C_6$)-alkyl, C(O)OH, C(O)$NH_2$, C(O)$NHCH_3$ or C(O)N($CH_3$)$_2$;

R4 is $(CH_2)_n$—R5, wherein n is 0–6;

R5 is phenyl, biphenylyl, 1- or 2-naphthyl, 2-, 3- or 4-pyridyl or 2- or 3-thienyl;

and R5 is substituted by
NH—$SO_2$—($C_1$–$C_6$)-alkyl, NH—$SO_2$-phenyl,
wherein the phenyl ring may be substituted up to two times by F, Cl, CN, OH, ($C_1$–$C_6$)-alkyl, O—($C_1$–$C_6$)-alkyl, $CF_3$, COOH, COO($C_1$–$C_6$)-alkyl, $CONH_2$;

$(CH_2)_n$—$SO_2$—$(C_1$–$C_6)$-alkyl, wherein n is 1–6, $(CH_2)_n$—$SO_2$—$NH_2$, $(CH_2)_m$—$SO_2$—NH—$(C_1$–$C_6)$-alkyl, $(CH_2)_m$—$SO_2$—N[$(C_1$–$C_6)$-alkyl]$_2$ or $(CH_2)_n$—$SO_2$—N(=CH—N(CH$_3)_2$), wherein m is 0–6;

and R5 may be further substituted by F, Cl, Br, OH, CF$_3$, CN, OCF$_3$, O—$(C_1$–$C_6)$-alkyl, $(C_1$–$C_6)$-alkyl, $(C_3$–$C_6)$-cycloalkyl, COOH, COO$(C_1$–$C_6)$-alkyl, COO$(C_3$–$C_6)$-cycloalkyl, CONH$_2$, CONH$(C_1$–$C_6)$-alkyl, CON[$(C_1$–$C_6)$-alkyl]$_2$, NH$_2$, NH—CO—$(C_1$–$C_6)$-alkyl, NH—CO-phenyl, $(CH_2)_n$-phenyl, O—$(CH_2)_n$-phenyl, S—$(CH_2)_n$-phenyl, $SO_2$—$(CH_2)_n$-phenyl, wherein n is 0–3;

and their physiologically acceptable salts and physiologically functional derivatives.

12. The method of claim 10 wherein

R1, R' are independently selected from H, F, Cl, Br, I, CF$_3$, NO$_2$, CN, COOH, COO$(C_1$–$C_6)$-alkyl, CONH$_2$, $(C_1$–$C_6)$-alkyl, $(C_2$–$C_6)$-alkenyl, $(C_2$–$C_6)$-alkynyl, O—$(C_1$–$C_6)$-alkyl, $SO_2$—NH$_2$, phenyl, O—$(CH_2)_n$-phenyl, wherein n is 0–6, wherein the phenyl rings can in each case be substituted one to 3 times by F, Cl, Br, I, OH, CF$_3$, NO$_2$, CN, OCF$_3$, O—$(C_1$–$C_6)$-alkyl, $(C_1$–$C_6)$-alkyl, NH$_2$, CONH$_2$;

R2 is H, $(C_1$–$C_6)$-alkyl, $(C_3$–$C_6)$-cycloalkyl, $(CH_2)_n$-biphenyl, C(O)—$(C_1$–$C_6)$-alkyl or C(O)—$(CH_2)_n$-phenyl, wherein n is 0–5 and in which phenyl can be substituted up to two times by Cl, F, CN, CF$_3$, $(C_1$–$C_3)$-alkyl, OH, O—$(C_1$–$C_6)$-alkyl;

R3 is H, $(C_1$–$C_6)$-alkyl, F, $(CH_2)_n$-phenyl, wherein n is 0–5 and in which phenyl can be substituted up to two times by Cl, F, CN, CF$_3$, $(C_1$–$C_3)$-alkyl, OH, O—$(C_1$–$C_6)$-alkyl; COO$(C_1$–$C_6)$-alkyl, C(O)OH or C(O)NH$_2$;

R4 is $(CH_2)_n$—R5, wherein n is 0–6; or

R5 is phenyl, 1- or 2-naphthyl;

and R5 is substituted by

NH—$SO_2$—$(C_1$–$C_6)$-alkyl, NH—$SO_2$-phenyl, wherein the phenyl ring can be substituted up to two times by F, Cl, CN, OH, $(C_1$–$C_6)$-alkyl, O—$(C_1$–$C_6)$-alkyl, CF$_3$, COOH, COO$(C_1$–$C_6)$-alkyl, CONH$_2$;

$(CH_2)_n$—$SO_2$—$(C_1$–$C_6)$-alkyl, wherein n is 1–6, $(CH_2)_m$—$SO_2$—NH$_2$, $(CH_2)_m$—$SO_2$—NH—$(C_1$–$C_6)$-alkyl, $(CH_2)_m$—$SO_2$—N[$(C_1$–$C_6)$-alkyl]$_2$ or (CH2)$_m$—SO2—N(=CH—N(CH3)2), wherein m is 0–6;

and R5 may further be substituted by F, Cl, Br, OH, CF$_3$, CN, OCF$_3$, O—$(C_1$–$C_6)$-alkyl, $(C_1$–$C_6)$-alkyl, COOH, COO$(C_1$–$C_6)$-alkyl, CONH$_2$, NH$_2$, NH—CO—$(C_1$–$C_6)$-alkyl, NH—CO-phenyl, $(CH_2)_n$-phenyl, O—$(CH_2)_n$-phenyl, $SO_2$—$(CH_2)_n$-phenyl, wherein n is 0–3;

and their physiologically acceptable salts.

* * * * *